United States Patent [19]
Goeke et al.

[11] 3,954,424
[45] May 4, 1976

[54] PROCESS FOR PRODUCING A METHANE-CONTAINING GAS AND ARRANGEMENT THEREFOR

[75] Inventors: Eberhard Goeke; Hermann Staege, both of Essen, Germany

[73] Assignee: Krupp-Koppers GmbH, Essen, Germany

[22] Filed: May 15, 1974

[21] Appl. No.: 470,030

[30] Foreign Application Priority Data
May 23, 1973 Germany............................ 2326234

[52] U.S. Cl. ............................... 48/215; 48/197 R; 48/212; 48/210; 260/449 M
[51] Int. Cl.² ............................................. C01B 2/16
[58] Field of Search.......... 48/210, 203, 101, 197 R, 48/202, 215, 214; 260/449 M

[56] References Cited
UNITED STATES PATENTS

| | | | |
|---|---|---|---|
| 3,531,267 | 9/1970 | Gould | 48/214 |
| 3,709,669 | 1/1973 | Marion et al. | 48/214 |
| 3,753,671 | 8/1973 | Leas et al. | 48/197 |
| 3,759,679 | 9/1973 | Franz et al. | 48/214 |

FOREIGN PATENTS OR APPLICATIONS

| | | | |
|---|---|---|---|
| 165,746 | 10/1955 | Australia | 260/449 M |

*Primary Examiner*—R. E. Serwin
*Attorney, Agent, or Firm*—Michael J. Striker

[57] ABSTRACT

The gaseous mixture obtained from the partial oxidation of coal and/or heavy oil is desulfurized. Thereafter, the gaseous mixture is admitted into a reactor wherein it simultaneously undergoes a conversion reaction and a methanization reaction. The reactions take place at a temperature between 280° and 500°C and at a pressure between 3 and 60 atmospheres in excess of atmospheric pressure. The reactions proceed catalytically in the presence of conventional catalysts. After having been subjected to the reactions, the gaseous mixture is conveyed to a scrubber for the removal of carbon dioxide. A gas containing at least 80 percent by volume of methane is obtained.

6 Claims, 3 Drawing Figures

PROCESS FOR PRODUCING A METHANE-CONTAINING GAS AND ARRANGEMENT THEREFOR

BACKGROUND OF THE INVENTION

The invention relates generally to methane and, more particularly, to a process and arrangement for the production of a methane-containing gas.

Gases having a high methane content may, for instance, find an application as exchange gases for natural gas. Recently, numerous proposals for the production of natural gas exchange gas have become known. The starting materials which may be used include coke-oven gas and liquid, low-boiling hydrocarbons such as, for example, benzine. In addition, however, coal and/or heavy oil may also be used as starting materials.

If the two last-mentioned materials are used, then it is advantageous when the starting material is initially subjected to a partial oxidation (gasification). This may be accomplished by known processes such as the Koppers-Totzek process, the Shell process or the Texaco process. Which process is most favorably used depends primarily on the type and character of the starting material to be gasified. Likewise, the composition of the gas obtained from the partial oxidation is dependent upon the starting material used. This is clarified by the following Table where a comparison is given of the composition of the gas of partial oxidation obtained from the gasification of coal and that of the gas of partial oxidation obtained from the gasification of heavy oil:

TABLE

| Gas Composition (percent by volume) | Starting Material Coal | Heavy Oil |
|---|---|---|
| $CO_2$ + $H_2S$ and other sulfur compounds | 10.0 | 5.0 |
| CO | 58.5 | 47.0 |
| $H_2$ | 30.0 | 46.5 |
| $CH_4$ | 0.5 | 0.5 |
| $N_2$ + Ar | 1.0 | 1.0 |

The partial oxidation gas is then usually subjected to a desulfurization during which sulfur compounds contained in the gas are removed therefrom in accordance with known processes. Following the desulfurization, it has heretofore been the practice to catalytically convert a portion of the carbon monoxide contained in the partial oxidation gas, which catalytic conversion proceeds according to the following equation in known manner:

$$CO + H_2O \rightarrow H_2 + CO_2 \qquad (1)$$

The carbon dioxide formed during this reaction may then, by known means, be removed from the process. For the desulfurization and conversion, there are now available the most diverse, reliably proven possibilities and combinations. For instance, the conversion may take place prior to the desulfurization since there are presently available both sulfur-resistant and sulfur-susceptible conversion catalysts.

Subsequent to the desulfurization and conversion, it has heretofore been the practice to subject the partial oxidation gas, which now has a more or less high carbon monoxide content and which has been more or less freed of carbon dioxide, to a methanization reaction which proceeds catalytically essentially according to the following equation:

$$CO + 3H_2 \rightarrow CH_4 + H_2O \qquad (2)$$

Simultaneously, the carbon dioxide still remaining in the gas is methanized according to the following equation:

$$CO_2 + 4H_2 \rightarrow CH_4 + 2H_2O \qquad (3)$$

The known procedures outlined above have certain disadvantages, however. Thus, on the one hand, large quantities of water vapor are required for the conversion reaction since, aside from the water vapor required for the conversion reaction itself, it is also necessary to provide large quantities of equilibrium water vapor. On the other hand, during the methanization reaction which follows the conversion reaction, there is produced water vapor which has heretofore remained unused and which it has been necessary to eventually condense out of the gas.

A process for the production of normal municipal gas is known from the German patent 1,085,287 wherein a gas of synthesis is simultaneously methanized and converted. This process operates with special sulfide catalysts obtained from the elements of the sixth group of the Periodic System and, as a result, the gas which is to undergo reaction must contain a minimum of 100 to 1000 milligrams of sulfur per $Nm^3$ of gas in the form of sulfur compounds. This process, however, does not achieve the objective of reducing the quantities of water vapor required. In contrast, it is unconditionally required that adequate quantities of additional water vapor be utilized. This is necessary so that, on the one hand, the equilibrium of the methanization reaction will not be displaced too far to the right, which would result in an undesired increase in the calorific value of the municipal gas produced, and so that, on the other hand, adequate quantities of water vapor are available for the conversion reaction.

SUMMARY OF THE INVENTION

It is, therefore, a general object of the invention to provide a novel process and arrangement for the production of methane-containing gases.

Another object of the invention is to provide a process and arrangement which permit methane-containing gases to be produced more economically than was possible heretofore.

A further object of the invention is to provide a process and arrangement which permit methane-containing gases to be produced with quantities of water vapor which are greatly reduced from those required until now.

An additional object of the invention is to provide a process and arrangement for the production of methane-containing gases which enable the expenditures required for apparatus to be reduced.

A concomitant object of the invention is to provide a process and arrangement for the processing of partial oxidation gases which enable such processing to be performed more economically than with the procedures outlined above.

Still another object of the invention is to provide a process and arrangement for the processing of partial oxidation gases which enable such processing to be performed more economically than with the procedures outlined above and which, in particular, enable the water vapor requirements and the outlays for apparatus to be reduced.

The foregoing objects, and others which will become apparent, are achieved in accordance with the invention. One feature of the invention resides in a process for the production of a methane-containing gas whereby it is possible to produce a gas having a methane content of at least 80 percent by volume. Such a gas may, by virtue of its high methane content, find an application as a natural gas exchange gas, for instance.

Briefly stated, the invention provides, in a process for the production of a methane-containing gas, particularly a gas containing at least 80 percent of volume of methane, for conveying a gaseous mixture along a flow path and desulfurizing the gaseous mixture in a first portion of the path. The gaseous mixture is subjected to a conversion reaction and a methanization reaction in a second portion of the path downstream of the first portion thereof so as to obtain a methane-enriched gas and the conversion and methanization reactions are effected substantially simultaneously.

The process for the production of a methane-containing gas containing at least 80 percent by volume of methane may proceed by partially oxidizing (gasifying) coal and/or heavy oil. The gas resulting from the partial oxidation may then be desulfurized, converted, methanized and subjected to a carbon dioxide wash or scrub. According to the invention, the desulfurized partial oxidation gas is subjected to a simultaneous conversion and methanization and this may be carried out at a temperature between about 280° and 500°C and at a pressure between about 3 and 60 atmospheres in excess of atmospheric pressure. It has been found that the process of the invention, that is, the conversion and methanization reactions, may advantageously be performed in the temperature range of substantially 350° to 400°C. The conversion and methanization reactions may proceed catalytically and, further in accordance with the invention, the transformation of the gas may occur in the presence of conventional conversion and methanization catalysts. It will, of course, be appreciated that the conversion and methanization catalysts to be utilized are those which are active at the particular temperature being used.

For carrying out the process according to the invention, the following conventional catalysts may, for example, be used: The known nickel catalysts may be utilized as methanization catalysts. Insofar as the conversion catalysts are concerned, there are two general types which come into consideration, namely, the so-called "normal temperature" catalysts and the so-called "low temperature" catalysts. The known iron oxide catalysts pose an example of the normal temperature catalysts. On the other hand, catalysts which include copper and zinc as active metals are examples of the low temperature catalysts. All of these catalysts are distributed in practice and are available without difficulty and are described in "Ullmann's Encyklopadie der technischen Chemie," 3rd Edition, Vol. 18, p. 519 and 4th Edition, Vol. 7, page 474.

The advantages of the invention over the prior art are readily apparent. Thus, according to the invention, the gas to be treated is first desulfurized and subsequently subjected to conversion and methanization reactions which may be carried out in the presence of conventional, readily available catalysts. In contrast, the process known from the above-mentioned German patent operates with special sulfide catalysts obtained from the elements of the sixth group of the Periodic System and the gas to be converted and methanized must have a minimum sulfur content, in the form of sulfur compounds, of 100 milligrams of sulfur per $Nm^3$ of gas. Moreover, by proceeding in accordance with the invention, the quantity of water vapor which must be supplied is reduced. On the other hand, the process of the above-mentioned German patent unconditionally requires that adequate quantities of additional water vapor be supplied in order that the equilibrium of the methanization reaction is not too far displaced to the right, which would result in an undesirable increase of the calorific value of the municipal gas to be produced by this process, and in order that adequate quantities of water vapor be available for the conversion reaction. The known process of the German patent does not, then, provide any suggestion which would lead to the process of the invention.

The invention also provides, in an arrangement for the production of a methane-containing gas, particularly a gas containing at least 80 percent by volume of methane, a combination which comprises means defining a flow path for a gaseous mixture and means for conveying the gaseous mixture along the flow path. Means is provided in the flow path for desulfurizing the gaseous mixture. The arrangement of the invention further includes means in the flow path downstream of the desulfurizing means for subjecting the gaseous mixture to a conversion reaction and a methanization reaction simultaneously so as to obtain a methane-enriched gas.

The means for subjecting the gaseous mixture to the conversion and methanization reactions may include a suitable reactor or suitable reactors. The conversion and methanization catalysts used for carrying out the process of the invention may be provided in such a reactor in form of a homogeneous mixture. However, it is also possible for the catalysts to be arranged separately from one another in the form of layers. It is further possible for the catalysts to be present in the form of homogeneous mixtures and to be arranged in the form of layers in which event the individual layers may be of different composition.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
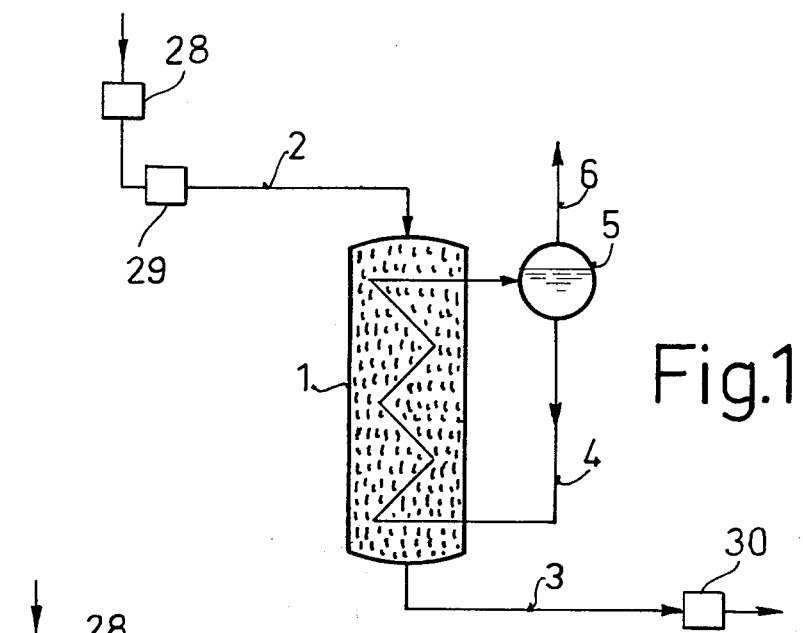
FIG. 1 is a diagrammatic representation of one form of an arrangement according to the invention which may be used for carrying out the process of the invention.

Referring first to FIG. 1, it is pointed out that there is here shown a so-called "isothermal" reactor which may advantageously be used for carrying out the process according to the invention. The reactor is indicated by reference numeral 1 and, as is represented by the dots or streaks in the reactor 1, the latter is practically completely filled with a homogeneous mixture of a conversion catalyst and a methanization catalyst. It should be mentioned here that wherever reference is made to conversion herein, this is intended to denote the reaction set forth by equation (1) whereas the term methanization is intended to denote the reactions set forth by equations (2) and (3).

A pump 28 or the like conveys a gaseous mixture to be transformed or treated towards the reactor 1 through a conduit 2. The gaseous mixture is here assumed to be the product of the partial oxidation of a carbonaceous substance such as, for example, coal and/or heavy oil. Before entering the reactor 1, the partial oxidation gas to be transformed passes through a device 29 in which it is at least partially desulfurized, that is, in which sulfur and/or sulfur compounds are at least partially removed from the gaseous mixture. After desulfurization, the gaseous mixture is conveyed into the reactor 1 wherein it simultaneously undergoes a conversion reaction and a methanization reaction which proceed catalytically. The gaseous mixture leaves the reactor 1 via a conduit 3 and the methane-enriched gas thus obtained may then be admitted into a scrubbing device 30 for the removal of at least part of the carbon dioxide contained herein.

A conduit system 4 is provided and is partially accommodated within the reactor 1. As illustrated, the conduit system 4 communicates with a high-pressure steam generator 5. The conduit system 4 may be filled with a suitable heat-exchange fluid such as, for instance, water.

The conversion and methanization reactions generate heat, that is, they are exothermic, and the provision of the conduit system 4 permits the temperature in the reactor 1 to be maintained substantially constant. In other words, the conduit system 4 makes it possible for the conversion and methanization reactions to proceed under substantially isothermal conditions. Thus, the heat of reaction which is liberated may be removed from the reactor 1 by heat-exchange with the water flowing in the conduit system 4. The liberated heat of reaction may then be used for the production of high-pressure steam in the steam generator 5. The steam produced may be removed from the latter via a conduit 6.

The arrangement illustrated in FIG. 1 may be modified in that the catalysts may be arranged in the reactor 1 in the form of layers as mentioned earlier. In such an event, it is possible for the conversion and methanization catalysts to be arranged separately in the reactor 1. On the other hand, it is also possible for the layers to comprise homogeneous mixtures of the conversion and methanization catalysts with the individual layers being of different composition.

The conversion and methanization reactions may be carried out at temperatures between about 280° and 500°C and the pressure in the reactor 1 may lie between about 3 and 60 atmospheres in excess of atmospheric pressure. A preferred temperature range for carrying out the reactions is 350° to 400°C.

Figure 2:
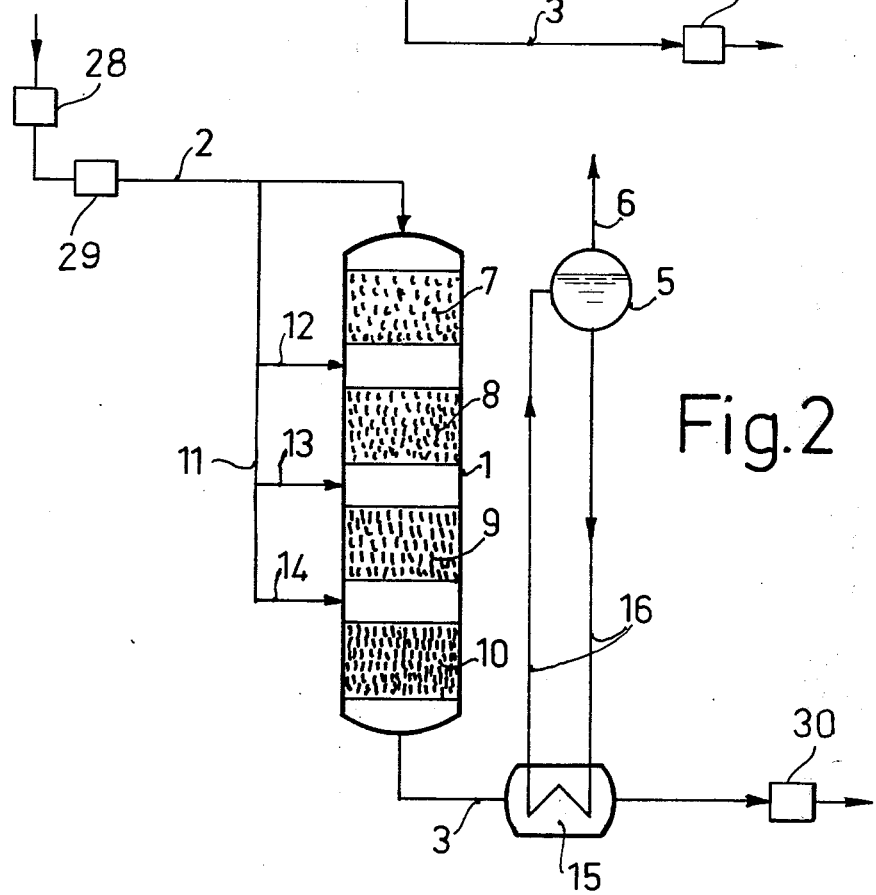
FIG. 2 is a diagrammatic representation of another form of an arrangement according to the invention which may be used for carrying out the process of the invention.

Referring now to FIG. 2, it may be seen that the same reference numerals as in FIG. 1 have been used to designate similar components where possible. In FIG. 2, the reactor 1 is constructed as a so-called "quench-type" reactor. In this embodiment, the conversion and methanization catalysts are arranged in the reactor 1 in the form of four different layers 7, 8, 9 and 10 which are situated one above the other. Although the layers 7–10 are here illustrated as comprising homogeneous mixtures of the conversion and methanization catalysts, it will be appreciated, as an example, that each or some of the layers 7–10 could, in turn, be made up of two layers one of which includes the conversion catalyst and the other of which includes the methanization catalyst. A space is provided between adjacent ones of the layers 7–10.

A conduit 11 branches off from the conduit 2 and, in turn, the conduit 11 branches off into the three conduits 12, 13 and 14. Each of the branch conduits 12–14 communicates with the reactor 1 at a location intermediate adjacent ones of the layers 7–10, that is, the branch conduits 12–14 communicate with the reactor 1 at the spaces defined between adjacent ones of the layers 7–10. In this manner, a portion of the partial oxidation gas flowing through the conduit 2 may be conveyed directly to the lower layers 8–10. It will be self-understood that valves and regulating devices may be provided in the conduit 11 and the corresponding branch conduits 12–14 by means of which the quantity of partial oxidation gas conveyed to the individual layers 7–10 of the catalyst bed may be precisely set and regulated.

By means of this arrangement, it is possible to compensate for the temperature increase in the individual layers of the catalyst bed which occurs due to the heat of reaction by the introduction of cold partial oxidation gas at intermediate locations of the catalyst bed.

In the present embodiment, the methane-containing gas leaving the reactor 1 via the conduit 3 flows into a waste-heat boiler 15 wherein it is subjected to indirect cooling. A coiled pipe or tube 16 is built into the boiler 15 and the pipe 16 in turn communicates with the high-pressure steam generator 5. As a result, the heat of reaction may here also be used for the production of high-pressure steam which latter is again withdrawn from the generator 5 via the conduit 6.

Figure 3:
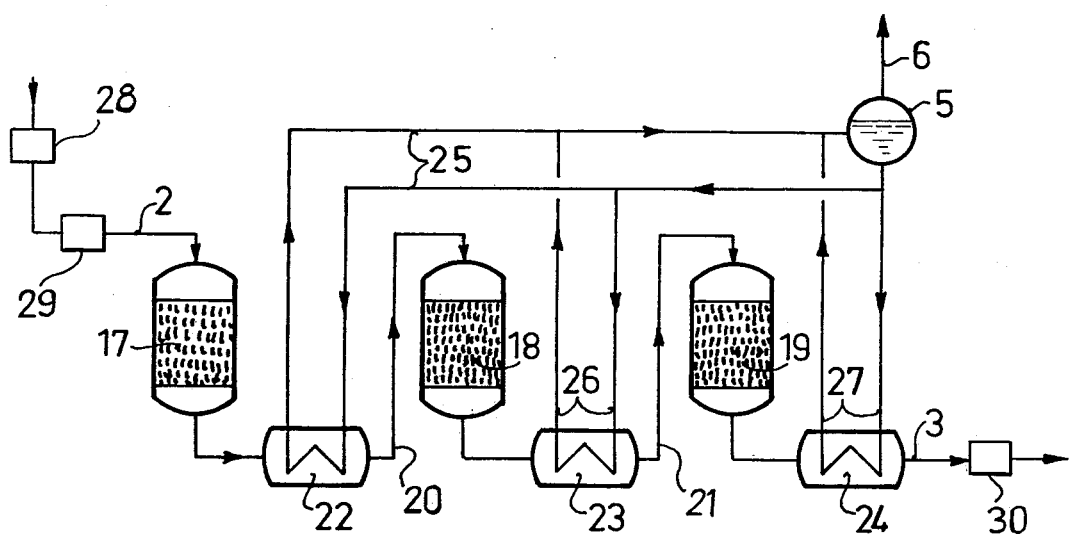
FIG. 3 is a diagrammatic representation of still another form of an arrangement according to the invention which may be used for carrying out the process of the invention.

The embodiment illustrated in FIG. 3 also operates with the indirect removal of the heat of reaction and, again, where possible, the same reference numerals as in the preceding FIGURES have been used to designate similar components. Here, instead of a single reaction chamber, the reactor includes a plurality of series-arranged reaction chambers 17, 18 and 19 which are filled with the conversion and methanization catalysts. It will be appreciated that, although the reaction chambers 17–19 are illustrated as being filled with homogeneous mixtures of the conversion and methanization catalysts, the conversion and methanization catalysts could be in the form of layers.

The reaction chambers 17 and 18 are connected by a conduit 20 whereas the reaction chambers 18 and 19 are connected by a conduit 21. The partial oxidation gas is again introduced into the reactor system via the conduit 2 and the thus-introduced gas flows in sequence through the reaction chambers 17–19 leaving the reactor system via the conduit 3. Waste-heat boilers 22 and 23 are provided, respectively, in the conduits 20 and 21 whereas a waste-heat boiler 24 is also provided in the conduit 3 so that the gas may be correspondingly cooled. Coiled pipes or tubes 25, 26 and 27 are built into the wasteheat boilers 22–24, respectively, and the pipes 25–27 are filled with a suitable heat-exchange fluid such as, for example, water. Each of the pipes 25–27 communicates with the high-pressure steam generator 5 in the manner illustrated. By virtue of this arrangement, the heat of reaction may here also be utilized for the production of high-pressure steam and the high-pressure steam generator in the generator 5 may again be withdrawn therefrom via the conduit 6.

The arrangement according to FIGS. 1 and 2, in particular, exhibit an unequivocal constructional simplification as opposed to the constructions for carrying out the known processes wherein the conversion and methanization are performed in apparatus which are discrete from one another.

The effects obtainable in accordance with the invention will be further illustrated below by two Examples which, however, are not to be construed as limiting the invention in any manner. The following represents the compositions of two gases, in volume percent, which are to be transformed or reacted in accordance with the invention and which were obtained by partial oxidation:

|  | EXAMPLE I (coal) | EXAMPLE II (heavy oil) |
| --- | --- | --- |
| $CO_2$ | 10.0 | 5.0 |
| CO | 58.5 | 47.0 |
| $H_2$ | 30.0 | 46.5 |
| $CH_4$ | 0.5 | 0.5 |
| $N_2$ | 1.0 | 1.0 |

The partial oxidation gas of Example I was obtained by the gasification of coal whereas the partial oxidation gas of Example II was obtained by the gasification of heavy oil. These gases were, in both instances, reacted in an isothermal reactor such as illustrated in FIG. 1 at a temperature of 350°C and a pressure of 15 atmospheres in excess of atmospheric pressure. A homogeneous mixture of a conventional conversion catalyst and a conventional methanization catalyst was used as the catalyst. The mixture filled the reactor 1 in the form of a loose mass. By means of the water circulating through the conduit system 4, the reaction temperature was held at the indicated value with small variations to either side. The gas leaving the reactor 1 via the conduit 3 had the following composition, again in terms of volume percent:

|  | Gas of Example I | Gas of Example II |
| --- | --- | --- |
| $CO_2$ | 64.6 | 52.1 |
| CO | 0.1 | 0.1 |
| $H_2$ | 3.8 | 4.5 |
| $CH_4$ | 30.1 | 41.5 |
| $N_2$ | 1.4 | 1.8 |

Subsequently, carbon dioxide was, in each case, removed from the gas in known manner by means of the scrubbing device 30. Thereafter, a methane-containing gas having the following respective compositions, in terms of volume percent, was obtained:

|  | Gas of Example I | Gas of Example II |
| --- | --- | --- |
| CO | 0.2 | 0.1 |
| $H_2$ | 10.9 | 9.9 |
| $CH_4$ | 85.0 | 86.8 |
| $N_2$ | 3.9 | 3.7 |

By virtue of their high methane content, these gases may, without difficulty, be used as exchange gases for natural gas. Furthermore, if necessary or desired, these gases may also still be subjected to a further after-treatment in known manner.

It will be understood that each of the elements described above, or two or more together, may also find a useful application in other types of arrangements and processes differing from the types described above.

While the invention has been illustrated and described as embodied in a process for producing a methane-containing gas and arrangement therefor, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A process of making a methane-rich gas from the gaseous product obtained in the partial oxidation of coal or heavy oil, the said process comprising substantially desulfurizing said gaseous product and then subjecting it to simultaneous conversion and methanization reactions, at a temperature between 280° and 500°C and a pressure of 3 to 60 atmospheres above atmospheric, the said two reactions being carried out in at least one common reaction chamber in the presence of separate conversion and methanization catalysts arranged in at least one fixed bed in said reaction chamber.

2. The process of claim 1 wherein the catalysts are present in said reaction chamber as a homogeneous mixture.

3. The process of claim 2 wherein the mixture of catalysts is arranged in a plurality of spaced layers, the said catalyst mixture being present in each of said layers.

4. The process of claim 1 wherein the two types of catalysts are arranged in said common reaction chamber in individual layers so that each layer contains only one of said catalyst types.

5. The process of claim 1 wherein there is a plurality of said common reaction chambers in each of which both types of catalysts are present in at least one fixed bed.

6. The process of claim 1 wherein said conversion catalyst is a catalyst in which the active material is selected from the group consisting of iron oxide, copper and zinc and wherein said methanization catalyst is a nickel catalyst.

* * * * *